United States Patent
Robbins et al.

(10) Patent No.: US 12,239,671 B2
(45) Date of Patent: Mar. 4, 2025

(54) EXTRACELLULAR VESICLES DERIVED FROM HUMAN LIVER STEM CELLS (HLSCS)

(71) Applicant: UNICYTE EV AG, Oberdorf (CH)

(72) Inventors: Paul Robbins, Minneapolis, MN (US); Giovanni Camussi, Turin (IT); Maria Beatriz Herrera Sanchez, Turin (IT)

(73) Assignee: UNICYTE EV AG, Oberdorf (CH)

( * ) Notice: Subject to any disclaimer, the term of this patent is extended or adjusted under 35 U.S.C. 154(b) by 656 days.

(21) Appl. No.: 17/617,036

(22) PCT Filed: Jun. 9, 2020

(86) PCT No.: PCT/EP2020/065986
§ 371 (c)(1),
(2) Date: Dec. 7, 2021

(87) PCT Pub. No.: WO2020/249567
PCT Pub. Date: Dec. 17, 2020

(65) Prior Publication Data
US 2022/0226389 A1   Jul. 21, 2022
US 2023/0037275 A2   Feb. 2, 2023

(30) Foreign Application Priority Data
Jun. 10, 2019 (EP) .................... 19179220

(51) Int. Cl.
*A61K 35/407* (2015.01)
*A61P 39/00* (2006.01)

(52) U.S. Cl.
CPC ............ *A61K 35/407* (2013.01); *A61P 39/00* (2018.01)

(58) Field of Classification Search
CPC .................................................. C12N 5/0672
See application file for complete search history.

(56) References Cited

FOREIGN PATENT DOCUMENTS

| WO | WO 2006/126236 | | 11/2006 |
|---|---|---|---|
| WO | WO 2017/189842 | | 11/2017 |
| WO | WO 2017/191234 | | 11/2017 |
| WO | WO-2017189842 A1 | * | 11/2017 |
| WO | WO 2020/030561 | | 2/2020 |

OTHER PUBLICATIONS

Tofino-Vian et al, Adipose tissue mesenchymal stem cell-derived extracellular vesicles as a biological therapy in osteoarthritic cells. Basic and Clinical Pharmacology and Toxicology, (2019) vol. 125, Supp. Supplement 4, pp. 22. Abstract No. O008. Meeting Info: 39th Congress of the Spanish Pharmacology Society. Las Palmas, Spain. Jul. 3, 2019-Jul. 5, 2019. (Year: 2019).*

Dmitrieva et al, High NaCl promotes cellular senescence. Cell cycle (Georgetown, Tex.), (Dec. 15, 2007) vol. 6, No. 24, pp. 3108-3113. Electronic Publication Date: Sep. 19, 2007 (Year: 2007).*

Herrera M B et al: 11 Human liver stem cell-derived microvesicles accelerate hepatic regeneration in hepatectomized rats, Journal of Cellular and Molecular Medicine, University Press Carol Davila, Bucharest, RO, vol. 14, No. 6B, Jun. 1, 2010 (Jun. 1, 2010), pp. 1605-1618, XP002730586, ISSN: 1582-1838, DOI: 10.1111/J.1582-4934.2009.00860.X.

Cristina Grange et al: "Stem cell-derived extracellular vesicles inhibit and revert fibrosis progression in a mouse model of diabetic nephropathy", Scientific Reports, vol. 9, No. I, Mar. 1, 2019 (Mar. 1, 2019), XP055643774, DOI: 10.1038/s41598-019-41100-9 the whole document.

Maria Beatriz Herrera Sanchez et al: "Extracellular vesicles from human liver stem cells restore argininosuccinate synthase deficiency", Stem Cell Research & Therapy, vol. 8, No. 1, Jul. 27, 2017 (Jul. 27, 2017), XP055643759, DOI: 10.1186/s13287-017-0628-9.

Maria Beatriz Herrera Sanchez et al: Human liver stem cells and derived extracellular vesicles improve recovery in a murine model of acute kidney injury, Stem Cell Research & Therapy, Biomed Central Ltd, London, UK, vol. 5, No. 6, Nov. 10, 2014 (Nov. 10, 2014), p. 124, XP021206650, ISSN: 1757-6512, DOI: 10.1186/SCRT514.

Tatiana Lopatina et al: "Extracellular vesicles from human liver stem cells inhibit tumor angiogenesis : HLSC extracellular vesicles inhibit tumor angiogenesis", International Journal of Cancer, vol. 144, No. 2, Oct. 22, 2018 (Oct. 22, 2018), pp. 322-333, XP055643777, ISSN: 0020-7136, DOI: 10.1002/ijc.31796.

Stefania Bruno et al: 11 Human Liver Stem Cell-Derived Extracellular Vesicles attenuate liver fibrosis and inflammation in a murine model of non-alcoholic steatohepatitis 11, Molecular Therapy, Oct. 1, 2019 (Oct. 1, 2019), XP055643788,. ISSN: 1525-0016, DOI: 10.1016/j.ymthe.2019.10.016.

McDaniel Kelly et al: 11 Stem Cell Derived Extracellular Vesicles Inhibits Liver Inflammation and Fibrosis in a Mouse Model of Primary Sclerosing Cholangitis 11, Gastroenterology : Official Publication of the American Gastroenterological Association, Williams & Wilkins, US, Apr. 22, 2017 (Apr. 22, 2017), XP085105062, ISSN: 0016-5085, DOI: 10.1016/S0016-5085(17)33602-8.

@E0126389.Bibliography for USA.
(from EP Priority)—Sato Keisaku et al (2017).
Hayflick, L. et al: "The Serial Cultivation of Human Diploid Cell Strains", Experimental Cell Research Dec. 1961; 25:585-621(61)9.
He, Shenghui et al: "Senescence in Health and Disease", Cell. Jun. 1, 2017;169(6):1000-1011.

(Continued)

*Primary Examiner* — Qiuwen Mi
(74) *Attorney, Agent, or Firm* — Kilyk & Bowersox, P.L.L.C.

(57) ABSTRACT

There is disclosed a preparation of extracellular vesicles derived from human liver stem cells, preferably from a non-oval human progenitor cell line that expresses hepatic cell markers, which is capable of reducing the senescence of a population of senescent cells, as measured in a SA-β-galactosidase-based cellular senescence assay. Also disclosed are therapeutic applications of the preparation of extracellular vesicles derived from human liver stem cells according to the invention. Therapeutic applications include the reduction of cellular senescence, e.g. in an vitro or ex vivo method, as well as the therapeutic treatment of diseases and conditions known to be related to ageing and cellular senescence, such as for example atherosclerosis, diabetes mellitus type 2, asthenia, and others.

3 Claims, 5 Drawing Sheets

(56) References Cited

OTHER PUBLICATIONS

Campisi, Judith: Aging, Cellular Senescence, and Cancer, Annual Rev Physiol. 2013; 75: 685-705.

Childs, Bennett et al, "Cellular senescence in aging and age-related disease: from mechanisms to therapy". Nat Med. Dec. 2015. 21(12):1424-1435.

Jeck, William et al, "Review: a meta-analysis of GWAS and age-associated diseases", Aging Cell. Oct. 2012: 11(5) 727-731.

Muñoz-Espín et al, "Cellular senescence: from physiology to pathology", Nature Reviews Molecular Cell Biology. Jul. 2014 15(7).

Van Deursen, Jan M., "The role of senescent cells in ageing", May 2014. Nature 509(7501): 439-446.

Dimri, Goberdhan P. et al., A biomarker that identifies senescent human cells in culture and in aging skin in vivo, Proceedings of the National Academy of Sciences of the United States of America, Sep. 1995, vol. 92, Issue 20, 1995, pp. 9363-9367.

Fuhrmann-Stroissnigg, Heike et al, "Identification of HSP90 inhibitors as a novel class of senolytics", Nature Communications, vol. 8:422, Sep. 4, 2017.

* cited by examiner

HLSC2-derived EVs (P6)

A)

B)

A)

B)

Comparison between human MSC-derived EVs and HLSC6B-derived EVs

A)

B)

Testing of HLSC-derived EVs from different passages

EXTRACELLULAR VESICLES DERIVED FROM HUMAN LIVER STEM CELLS (HLSCS)

FIELD OF THE INVENTION

The present invention relates to preparations of extracellular vesicles derived from stem cells for reducing cellular senescence and for treating senescence-related diseases and conditions.

BACKGROUND ART

Vesicular-mediated communication between cells appears critical in many biological processes. Small vesicles released from cells have recently emerged as important mediators of inter-cellular communication. These vesicles, that have been termed "extracellular vesicles (EVs)", are inclusive of exosomes released from the endosomal cell-membrane compartment and of microvesicles released from the cell surface by plasma membrane budding. The EV content of proteins, lipids and nucleic acids varies with the cell of origin and, after incorporation into recipient cells, they may transfer information which may change the phenotype and function of recipient cells.

Cellular senescence is a phenomenon by which cells cease to divide. Over the last few decades, this phenomenon has emerged as an important contributor to aging and age-related diseases and conditions. The available evidence suggests that senescence causes a loss of tissue-repair capacity because of cell cycle arrest in progenitor cells. Furthermore, senescent cells produce pro-inflammatory and matrix-degrading molecules in the so-called senescence-associated secretory phenotype (SASP). Accordingly, cellular senescence has become an attractive target for therapeutic exploitation.

Drugs able to kill senescent cells specifically in cell culture, termed senolytics, are able to reduce cellular senescence in vivo and to counteract ageing and age-related diseases and conditions. A number of senolytics are known in the prior art, including HSP90 inhibitors, Bcl-2 family inhibitors, piperlongumine, a FOXO4 inhibitory peptide and the combination of Dasatinib/Quercetin. Furthermore, International patent application WO 2017/189842 discloses a method for treating a patient suffering from a disease or condition caused by stem cell dysfunction or increased senescence, comprising administering to the patient a composition comprising extracellular vesicles (EVs) obtained from stem cells of a subject who is younger or healthier than the patient to be treated. WO 2017/189842 specifically mentions mesenchymal stem cells as the source for extracellular vesicles.

SUMMARY OF THE INVENTION

The present inventors have now surprisingly found that extracellular vesicles derived from human liver stem cells are much more effective in reducing cellular senescence than extracellular vesicles derived from mesenchymal stem cells (MSCs).

Accordingly, a first aspect of the present invention is a preparation of extracellular vesicles derived from human liver stem cells, which is capable of strongly reducing cellular senescence.

A second aspect of the present invention is a preparation of extracellular vesicles derived from human liver stem cells for use in the therapeutic treatment of cellular senescence or a cellular senescence-related disease or condition.

A third aspect of the present invention is an in vitro or ex vivo method of reducing cellular senescence in a cell-containing biological sample, comprising contacting the cell-containing biological sample with a preparation of extracellular vesicles derived from human liver stem cells A fourth aspect of the present invention is a method of reducing cellular senescence in a subject in need thereof, comprising administering to the subject an effective amount of a preparation of extracellular vesicles derived from human liver stem cells.

A fifth aspect of the present invention is a method of treating a cellular senescence-related disease or condition in a subject in need thereof, comprising administering to the subject an effective amount of a preparation of extracellular vesicles derived from human liver stem cells.

A sixth aspect of the present invention is a method of manufacturing a pharmaceutical preparation of extracellular vesicles derived from human liver stem cells, the preparation being capable of strongly reducing cellular senescence. The method according to the sixth aspect of the invention comprises the following steps:

(a) isolating EVs from multiple preparations of a body fluid or from the conditioned medium of a cell culture;
(b) preparing one or more samples from the isolated EVs at a predetermined concentration of EVs;
(c) testing the activity of each EVs sample in a potency test measuring the reduction of cellular senescence, wherein senescence is measured in a SA-β-galactosidase-based cellular senescence assay using as the control the test senescent cells not treated with EVs; and
(d) selecting the preparations in which the reduction of cellular senescence measured exceeds a predetermined threshold.

Optionally, the method of the invention further includes pooling two or more of the preparations selected in step (d).

DETAILED DESCRIPTION OF THE INVENTION

Figure 1:
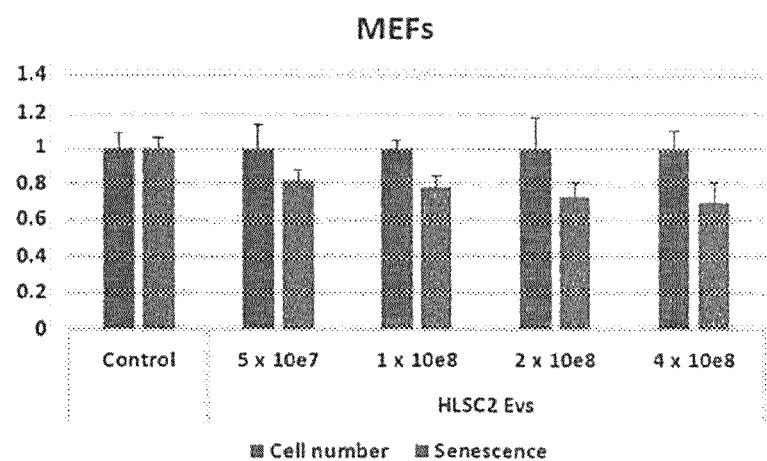
FIG. 1 shows the reduction of senescence obtained by treating MEFs (FIG. 1A) and IMR90 cells (FIG. 1B) with different concentrations of extracellular vesicles (EVs) derived from human liver stem cells obtained from a 70 years donor and taken from passage 6 (HLSC2 (P6)). The control are untreated cells. Senescence was measured by a SA-β-galactosidase-based cellular senescence assay.
Figure 1:
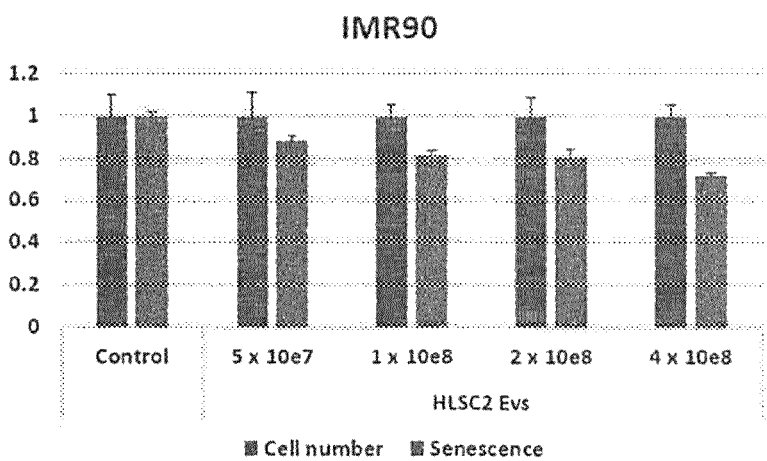

The invention is based on the discovery that extracellular vesicles derived from human liver stem cells are able to reduce cellular senescence, independently of the age of the donor and of the cell passage from which they are obtained. This is a surprising discovery vis-à-vis the teachings of WO 2017/189842, which discloses that conditioned media from young, but not old stem cells, can reverse senescence in fibroblasts and aged stem cells. Moreover, WO 2017/189842 mentions mesenchymal stem cells as the EVs source, while the present inventors found that EVs derived from human liver stem cells are much more effective in reducing cellular senescence than extracellular vesicles derived from mesenchymal stem cells (MSCs).

One advantage of using extracellular vesicles as senolytics derives from the fact that extracellular vesicles are natural products. In addition, as shown in the examples, human liver stem cells are easily isolated and extracellular vesicles are readily purified from the isolated human liver stem cells. Extracellular vesicles have been shown to preferentially target damaged, senescent cells, which makes them a particularly effective tool for reducing cellular senescence and treating diseases and conditions caused by cell damage and senescence.

Cellular senescence was described for the first time in Hayflick, L. & Moorhead, P. S. The serial cultivation of human diploid cell strains. Exp Cell Res. 25 585-621, (1961). Senescent cells do not proliferate despite the presence of nutrients, growth factors and absence of contact inhibition, but remain metabolically active. This phenomenon is known as "replicative senescence" and was mainly attributed to telomere shortening. Further studies have shown that senescence can also be induced by other stimuli, such as oncogenic stress, DNA damage, cytotoxic drugs and irradiation. Under certain circumstances, cell senescence may be beneficial as it acts as a tumor suppressor. However, senescence increases with aging due to the accumulation of cellular damage. Senescent cells secrete cytokines, metalloproteinases and growth factors, which constitute the so-called senescence-associated secretory phenotype (SASP). This age-dependent increase in cellular senescence and SASP contributes to decreased tissue homeostasis and aging. Additionally, the age-dependent increase in senescence burden may be responsible for numerous age-related diseases and conditions.

The relationship between cellular senescence and a number of diseases and conditions is known in the prior art. Known senescence-related diseases and conditions include for example atherosclerosis, diabetes mellitus type 2, asthenia, hair graying, skin-ageing, sarcopenia, age-related adiposity, fibrosis and in particular pulmonary fibrosis, glaucoma, cataracts, diabetic pancreas, osteoarthritis, degenerated intervertebral discs, cancer, pulmonary hypertension, age-related cardiovascular disease, age-related neurodegeneration, age-related cognitive impairment, Alzheimer's disease, Parkinson's disease, macular degeneration, chronic obstructive pulmonary disorder, emphysema, insulin insensitivity (see, inter alia, He S, Sharpless N E. Senescence in Health and Disease. Cell. 2017; 169(6):1000-1011; Campisi J. Aging, cellular senescence, and cancer. Annu Rev Physiol. 2012; 75:685-705; Childs B G, Durik M, Baker D J, van Deursen J M. Cellular senescence in aging and age-related disease: from mechanisms to therapy. Nat Med. 2015; 21(12):1424-1435; Jeck W R, Siebold A P, Sharpless N E. Review: a meta-analysis of GWAS and age-associated diseases. Aging Cell. 2012; 11(5):727-731; Muñoz-Espin, D. and Serrano, M. Cellular senescence: from physiology to pathology. Nat. Rev. Mol. Cell Biol. 2014; 15: 482-496; van Deursen J M. The role of senescent cells in ageing. Nature. 2014; 509(7501):439-446).

Accordingly, extracellular vesicles derived from human liver stem cells are particularly suitable for reducing cellular senescence and treating the aforementioned senescence-related diseases and conditions.

A particularly preferred type of liver stem cells for use as the EVs source within the context of the present invention is the non-oval human liver pluripotent progenitor cell line expressing hepatic cell markers described in International patent application WO2006/126236. International patent application WO2006/126236 also discloses a method of isolating the aforementioned non-oval human liver pluripotent progenitor cell line. The human non-oval human liver pluripotent progenitor cell line of WO2006/126236 (designated as HLSCs in the present description) and the method for preparing HLSCs are hereby incorporated by reference.

In a preferred embodiment, the non-oval human liver pluripotent progenitor cell line is capable of differentiating into mature liver cells, insulin producing cells, osteogenic cells and epithelial cells. In a further preferred embodiment, the non-oval human liver pluripotent progenitor cell line expresses the hepatic cell marker albumin and the stem cell markers CD44, CD73, and CD90 and does not express the cell markers CD117, CD34, and CD45.

Next to the type of stem cell source the age of the patient and the general health status influences the capability of the EV preparation to reduce cellular senescence. While it was shown that EVs taken from a patient at the age of 70 are still effective, a higher efficacy is associated with EVs derived from stem cells from patients of a younger age. It is preferred that the EVs are obtained from a stem cell source from patients of up to 25 years of age. Furthermore, a higher number of culture passages of the stem cells the EVs are derived from decreases the capability of the EV preparation to reduce cellular senescence. While preparations of EVs taken from a HLSC culture at passage 10 still shows a significant senescence-reducing activity, an EV preparation taken from a HLSC culture at less than 10 passages is preferred.

Numerous markers are available for measuring cellular senescence, but the current standard for detecting senescent cells is the measurement of a specific β-galactosidase enzymatic activity at pH 6 (Dimri G P, Lee X H, Basile G, Acosta M, Scott C, Roskelley C et al. A biomarker that identifies senescent human-cells in culture and in aging skin in-vivo. Proc Natl Acad Sci USA 1995; 92: 9363-9367). Advantageously, SA-β-gal is a recognized marker for all types of senescent cells, whereby the SA-β-gal assay can be used for the assessment of the senescence of any type of cells.

According to the general SA-β-galactosidase-based cellular senescence assay, a cell sample to be assayed is incubated in a culture medium, then contacted with a DNA intercalating dye, such as Hoechst dye. SA-β-gal-positive cells are then quantified by routine methods, such as by sCMOS camera detection technology.

As mentioned, the SA-β-galactosidase-based cellular senescence assay can be performed with different cell types. Well recognized cell types for performing the SA-β-gal cellular senescence assay are human IMR90 fibroblasts with etoposide-induced senescence and primary Erc1$^{-/-}$ murine embryonic fibroblasts (MEFs) with oxidative stress-induced senescence, both described in Fuhrmann-Stroissnigg, H. et al. Identification of HSP90 inhibitors as a novel class of senolytics. *Nat Commun.* 8 (1), 422, (2017).

In an experimental study carried out using the aforementioned types of SA-β-galactosidase-based cellular senescence assays, the present inventors found that the EVs derived from human hepatic stem cells are particularly effective in reducing the senescence of cells as compared to umbilical cord MSC-derived EVs. Particularly preferred EVs for this purpose are EVs derived from the non-oval human liver pluripotent progenitor cell line expressing hepatic cell markers disclosed in WO2006/126236.

Furthermore, by using the aforementioned types of the SA-β-galactosidase-based cellular senescence assays, the present inventors obtained a preparation of EVs derived from human hepatic stem cells having a particularly strong senescence-reducing activity. Indeed, the inventors found that such a preparation of EVs is capable of reducing the senescence of a population of senescent cells by about 10% when employed at a concentration of $2.5 \times 10^7$ EVs/ml. At a dose of about $2 \times 10^8$ EVs/ml, the preparation of the invention was shown to reduce senescence by about 40%.

Based on the strong senescence-reducing activity of preparations of EVs derived from human hepatic stem cells, EV preparations at a concentration of $2 \times 10^8$ EVs/ml according to the invention show a reduction of senescence of a population of test senescent cells by at least 10%, wherein senescence is measured in a SA-β-galactosidase-based cellular senescence assay using as the control the test senescent cells not treated with EVs. In preferred embodiments, EV preparations at a concentration of $2 \times 10^8$ EVs/ml show a reduction of senescence of at least 25%, more preferably 40%. In another further embodiment a preparation of a lesser concentration of $2.5 \times 10^7$ EVs/ml show a reduction of senescence of at least 7%, more preferably 10%.

Interestingly, the senescence-reducing activity of the EVs preparation of the invention is present, although with a reduced strength, even when the extracellular vesicles are derived from an old donor (i.e. 70 years old) or when the extracellular vesicles are purified from cells kept in culture for an extended period of time, for example for up to passage 10.

EXAMPLES

Isolation of Human Liver Stem Cell (HLSCs)

HLSCs were isolated from human cryopreserved normal adult hepatocytes (Lonza, Basel, Switzerland) as described before (Herrera Sanchez M B, Bruno S, Grange C, Tapparo M, Cantaluppi V, Tetta C, et al. Human liver stem cells and derived extracellular vesicles improve recovery in a murine model of acute kidney injury. *Stem Cell Res Ther* (2014) 5(6):124).

Briefly, HLSC6B and HLSC2 were cultured in alpha minimum essential medium (Lonza, Basel, Switzerland) supplemented with L-glutamine (5 mM), penicillin (50 Wimp, streptomycin (50 µg/ml) (all from Sigma, St. Louis, MO, USA), 10% fetal calf serum (FCS) (Invitrogen, Carlsbad, CA, USA) and human recombinant epidermal growth factor (rhEGF) and basic fibroblast growth factor (bFGF) (4 ng/ml both). Cells were expanded, characterized, and cryopreserved as described previously. Two days before extracellular vesicles (EVs) isolation, HLSCs were culture in culture medium where FCS was substituted with EVs-depleted FCS to avoid serum EVs contaminations.

Isolation of Extracellular Vesicles (EVs)

Extracellular vesicles (EVs) were obtained from supernatants of HLSC6b and HLSC2 (2×106 cells/T75 flask) cultured in serum-free Roswell Park Memorial Institute Medium (RPMI) (Euroclone S.p.A, Italy) for 18 h. Viability of cells at the time of supernatant collection was 98% as confirmed by Trypan blue exclusion. Briefly, supernatants were centrifuged at 3,000 g for 15 min at 4° C. for the removal of cell debris and apoptotic bodies, followed by ultracentrifugation at 100,000 g for 2 h at 4° C. (Beckman Coulter Optima L-90 K, Fullerton, CA, USA). The pellet of EVs obtained was resuspended in RPMI supplemented with 1% dimethyl sulfoxide (DMSO) and stored at −80° C. until use (Herrera Sanchez M B, Previdi S, Bruno S, Fonsato V, Deregibus M C, Kholia S, et al. Extracellular vesicles from human liver stem cells restore argininosuccinate synthase deficiency. Stem Cell Res Ther (2017) 8(1):176).

MEF Assay

The Ercc1$^{-/-}$ MEFs were isolated as disclosed in Fuhrmann-Stroissnigg, H. et al. Identification of HSP90 inhibitors as a novel class of senolytics. *Nat Commun.* 8 (1), 422, (2017). The MEF assay was performed essentially as disclosed in the same article. In brief, MEFs ($5 \times 10^3$) at 20% $O_2$ were seeded per well in 96-well plates at least 6 h prior to treatment. Following addition of the EVs, the MEFs were incubated for 24 to 48 h under 20% 02 oxygen conditions. For fluorescence analysis of SA-β-Gal activity, cells were washed 1× with PBS, Cl2FDG (10 µM) was added to the culture medium, and the cells were incubated for 1.5-2 h. Ten minutes prior to analysis, the DNA intercalating Hoechst dye (2 µg/ml) was added to the cells. For quantitative analysis of cell number (Hoechst staining) and number of C12FDG positive, senescent cells, a laser-based line scanning confocal imager IN Cell Analyzer 6000 with large field-of view sCMOS camera detection technology was used. An acquisition protocol was established using Acquisition software v4.5, including parameters such as the plates and wells that were imaged, wavelengths, and exposure time. The acquired images were analyzed using the Multi Target Analysis Module that allows the creation of various decision trees and the application of appropriate classification filters to different image stacks. All samples were analyzed in duplicate with 3-5 fields per well and mean values and standard deviations being calculated accordingly.

IMR90 Lung Fibroblasts

Human IMR90 lung fibroblasts were obtained from American Type Culture Collection (ATCC) and cultured in EMEM medium with 10% FBS and pen/strep antibiotics. To induce senescence, cells were treated for 24 h with 20 µM etoposide. Two days after etoposide removal, about 70% of IMR90 cells tested SA-β-Gal positive. Cells were treated for 48 h with 100 nM 17-DMAG and the percentage of SA-β-Gal-positive cells was determined using C12FDG-based senescence assay. This assay is disclosed in Fuhrmann-Stroissnigg, H. et al. Identification of HSP90 inhibitors as a novel class of senolytics. *Nat Commun.* 8 (1), 422, (2017).

Results

The experimental studies illustrated above were performed with extracellular vesicles derived from human liver stem cells obtained from a 15 years old donor (HLSC6B) and with extracellular vesicles derived from human liver stem cells obtained from a 70 years old donor (HLSC2).

Figure 2:
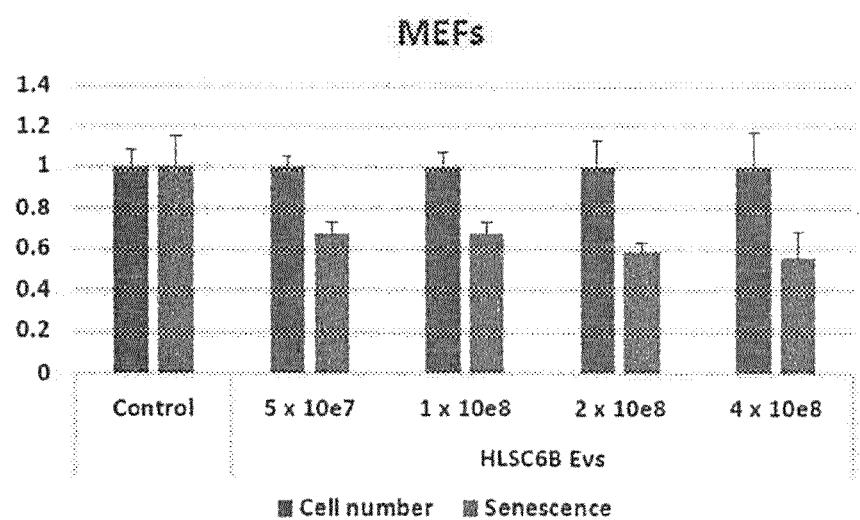
FIG. 2 shows the reduction of senescence obtained by treating MEFs (FIG. 1A) and IMR90 cells (FIG. 1B) with different concentrations of extracellular vesicles (EVs) derived from human liver stem cells obtained from a 15 years donor and taken from passage 4 (HLSC6B (P4)). The control are untreated cells. Senescence was measured by the SA-β-galactosidase-based cellular senescence assay.
Figure 2:
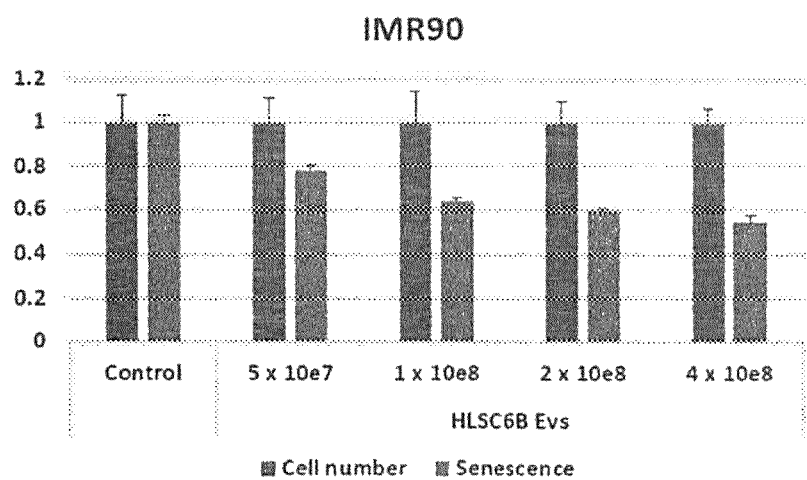
Figure 3:
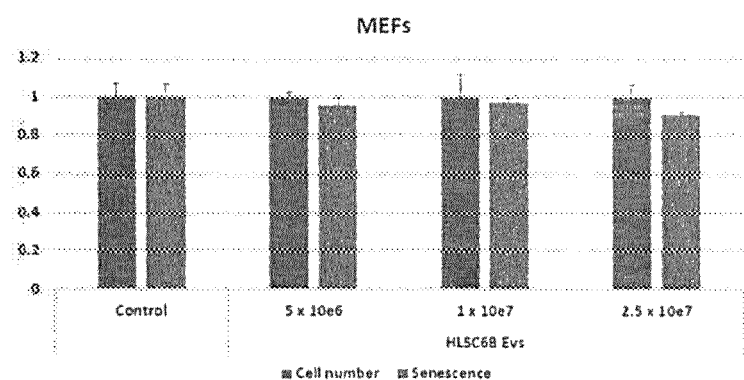
FIG. 3 shows the reduction of senescence obtained by treating MEFs with the extracellular vesicles (EVs) of FIG. 2 at lower concentrations. The control are untreated cells. Senescence was measured by a SA-β-galactosidase-based cellular senescence assay.
Figure 4:
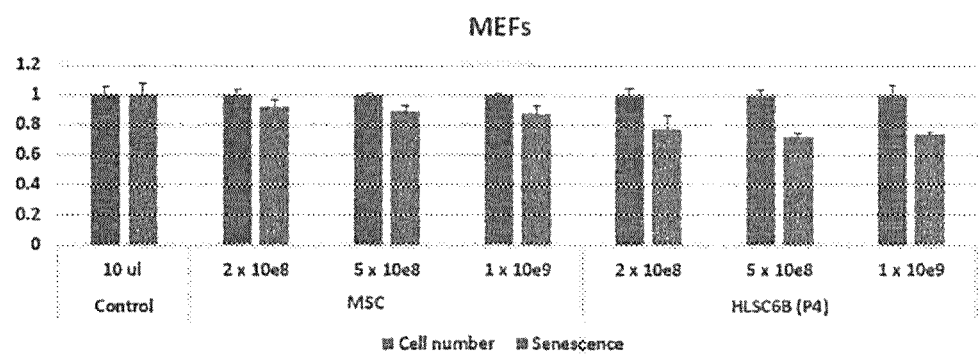
FIG. 4 is a comparison between the senescence-reducing activity of human umbilical cord MSC-derived EVs taken from passage 5 and HLSC6B-derived EVs tested on MEFs by a SA-β-galactosidase-based cellular senescence assay.
Figure 4:
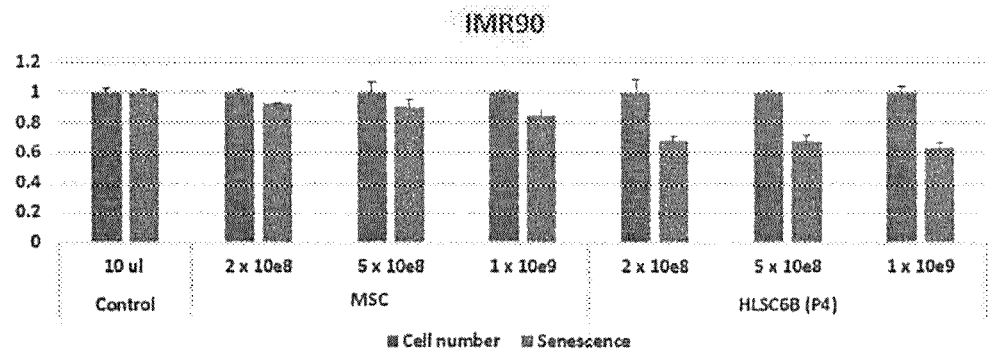

The experimental data show that both the HLSC6B-derived EVs and the HLSC2-derived EVs are able to reduce the percent of senescent IMR90 and MEFs cells in a reproducible manner (see FIGS. 1A, B FIG. 2A, B). FIG. 3 shows that a senescence-reducing activity of HLSC6B-derived EVs is already noticeable at a low concentration of $2.5 \times 10^7$ EVs/ml. HLSC6B-derived EVs are more effective than HLSC2-derived EVs in reducing fibroblast cellular senescence in both the MIF and the IMR90 assay, but both types of HLSC-derived EVs are in any case more effective than umbilical cord MSC-derived EVs (see Figure A, B and FIG. 1A, B).

Figure 5:
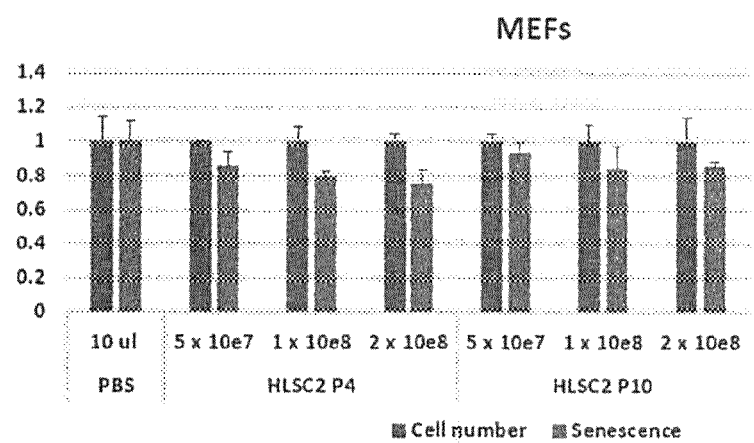
FIG. 5 shows the reduction of senescence obtained by treating MEFs with different concentrations of HLSC2-derived EVs and HLSC6B-derived EVs taken at 4 and 10 passages. Senescence was measured by the SA-β-galactosidase-based cellular senescence assay.
Figure 5:
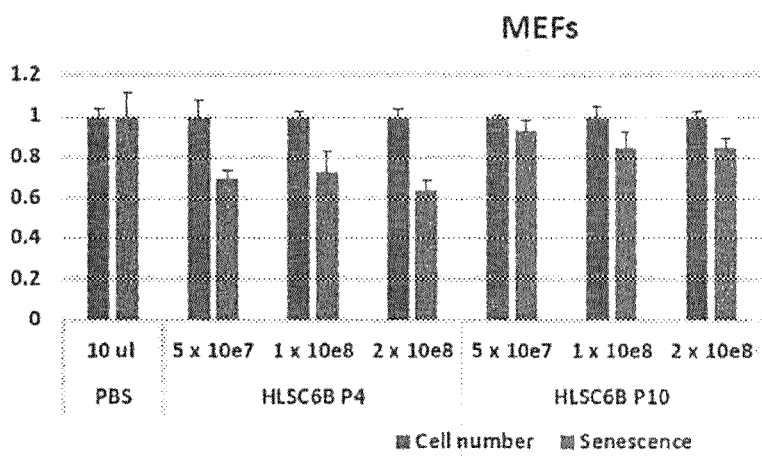

Furthermore, the experimental show that, although the ability of HLSC-derived EVs to suppress senescence diminishes with passage, this ability is still observed at passage 15 and is statistically significant at passage 10 both in the case of HLSC6B-derived EVs and in the case of HLSC2-derived EVs (see FIG. 5).

In the Figures, "cell number" indicates the senescence level measured for the control cells (i.e. not treated with the EVs), which is normalized to 1.

The invention claimed is:

1. A method of manufacturing a pharmaceutical preparation of extracellular vesicles (EVs) derived from human liver stem cells, comprising the steps of:
    isolating EVs from multiple preparations of a body fluid or from the conditioned medium of a cell culture;
    preparing one or more samples from the isolated EVs at a predetermined concentration of EVs;
    testing the activity of each EVs sample in a potency test measuring the reduction of cellular senescence wherein senescence is measured in a SA-β-galactosidase-based cellular senescence assay using test senescent cells not treated with EVs as a control;
    selecting the preparations in which the reduction of cellular senescence measured exceeds a predetermined threshold; and
    pooling two or more selected preparations, wherein preparations selected at a concentration of $2.5 \times 10^7$ EVs/ml reduce the senescence of a population of test senescent cells by at least 10%.

2. A method according to claim 1, wherein the preparations selected at a concentration of $2.5 \times 10^7$ EVs/ml reduce the senescence of a population of test senescent cells by at least 40%.

3. A method according to claim 1, wherein the SA-β-galactosidase-based cellular senescence assay is performed on primary mouse embryonic fibroblasts (MEFs) with oxidative stress-induced senescence, or on a human lung fibroblast cell line with etoposide-induced senescence.

* * * * *